(12) United States Patent
Alyaser

(10) Patent No.: US 8,680,163 B2
(45) Date of Patent: Mar. 25, 2014

(54) SYSTEM AND METHOD FOR PROVIDING AN INTEGRATED REACTOR

(75) Inventor: Abdelmonem Hussien Alyaser, San Jose, CA (US)

(73) Assignee: Enventix, Inc., San Jose, CA (US)

( * ) Notice: Subject to any disclaimer, the term of this patent is extended or adjusted under 35 U.S.C. 154(b) by 150 days.

(21) Appl. No.: 13/437,761

(22) Filed: Apr. 2, 2012

(65) Prior Publication Data

US 2012/0196943 A1 Aug. 2, 2012

Related U.S. Application Data

(63) Continuation of application No. 12/688,667, filed on Jan. 15, 2010, now Pat. No. 8,168,144.

(60) Provisional application No. 61/144,990, filed on Jan. 15, 2009.

(51) Int. Cl.
*C07C 27/00* (2006.01)

(52) U.S. Cl.
USPC .......................................... 518/702; 48/197 R

(58) Field of Classification Search
USPC .......................................... 518/702; 48/197 R
See application file for complete search history.

(56) References Cited

U.S. PATENT DOCUMENTS

| | | | |
|---|---|---|---|
| 3,489,206 A | 1/1970 | Lecourt | |
| 3,859,230 A | 1/1975 | Moe | |
| 4,196,894 A | 4/1980 | Brezny | |
| 5,070,016 A | 12/1991 | Hallberg | |
| 5,458,857 A | 10/1995 | Collins et al. | |
| 5,565,009 A | 10/1996 | Ruhl et al. | |
| 5,769,909 A | 6/1998 | Bonk et al. | |
| 6,238,815 B1 | 5/2001 | Skala et al. | |
| 6,245,303 B1 | 6/2001 | Bentley et al. | |
| 6,468,480 B1 | 10/2002 | Clawson et al. | |
| 6,790,431 B2 | 9/2004 | Wang et al. | |
| 6,821,501 B2 | 11/2004 | Matzakos et al. | |
| 7,367,996 B2 | 5/2008 | Clawson et al. | |
| 7,500,999 B2 | 3/2009 | Aaron et al. | |
| 2004/0013586 A1 * | 1/2004 | Oh et al. | 422/190 |
| 2005/0087437 A1 | 4/2005 | Sakurai et al. | |
| 2006/0045828 A1 | 3/2006 | Aaron et al. | |
| 2007/0158451 A1 | 7/2007 | Mao et al. | |
| 2008/0202028 A1 | 8/2008 | Tsangaris et al. | |
| 2008/0307703 A1 | 12/2008 | Dietenberger et al. | |

OTHER PUBLICATIONS

WO PCT/US2010/021265—Search Report, Mar. 2, 2010.

* cited by examiner

*Primary Examiner* — Walter D Griffin
*Assistant Examiner* — Huy-Tram Nguyen
(74) *Attorney, Agent, or Firm* — Orrick, Herrington & Sutcliffe LLP

(57) ABSTRACT

A system and method for providing an integrated indirectly fired reactor and steam generator are disclosed. According to one embodiment, the reactor comprises an indirect heating zone heating water and generating steam, a mixing zone mixing feedstock and the steam and providing a mixture of the feedstock and the steam, and a reaction zone comprising a first reactor and a second reactor. The first reactor converts the mixture to a first syngas at a first temperature. The second reactor converts the first syngas to a second syngas at a second temperature, the second temperature being higher than the first temperature.

23 Claims, 6 Drawing Sheets

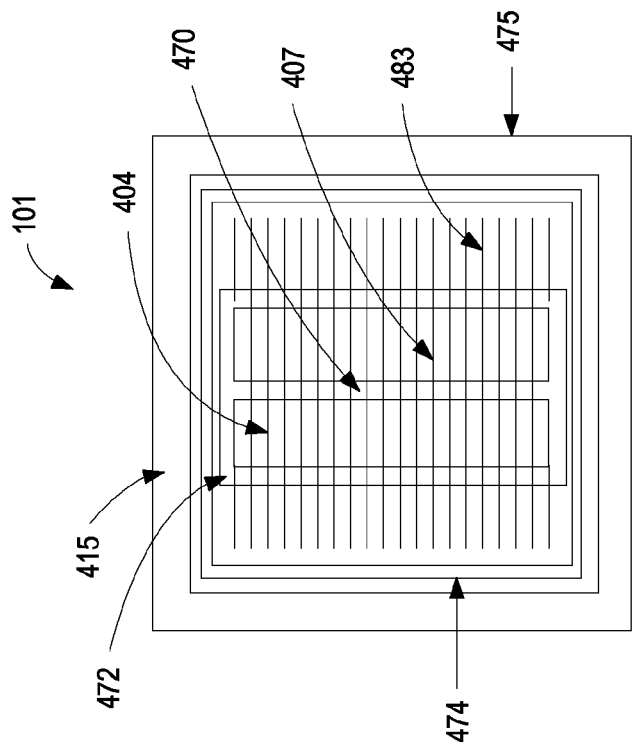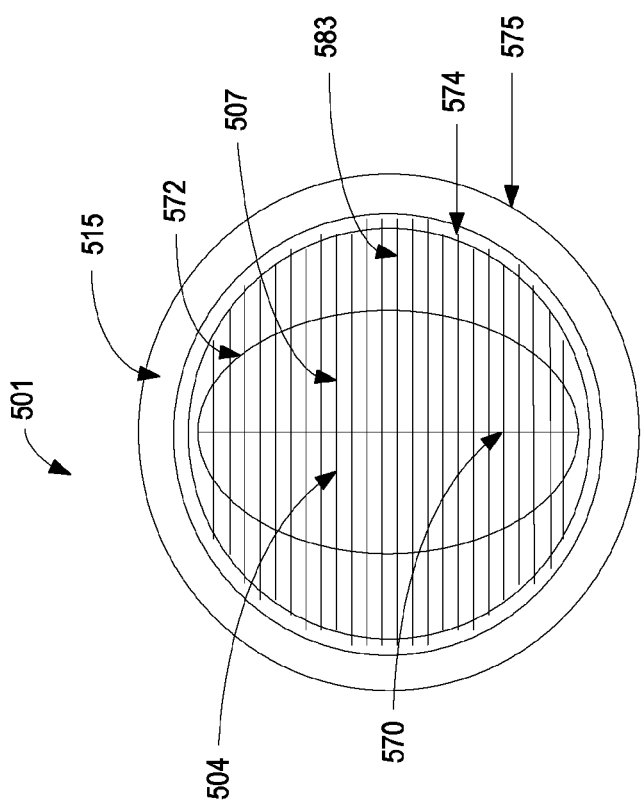
Fig. 5B
Fig. 5A

SYSTEM AND METHOD FOR PROVIDING AN INTEGRATED REACTOR

The present application is a continuation of U.S. patent application Ser. No. 12/688,667 titled "SYSTEM AND METHOD FOR PROVIDING AN INTEGRATED REACTOR," filed on Jan. 15, 2010, now U.S. Pat. No. 8,168,144 B2 which claims the benefit of and priority to U.S. Provisional Patent Application Ser. No. 61/144,990 filed on Jan. 15, 2009, both of which are hereby incorporated by reference herein in their entirety for all purposes.

FIELD

The present application relates to a system and method for generating power and/or producing synthetic chemicals. More particularly, the present invention is a system and method for providing an integrated reactor.

BACKGROUND

Global climate change and the contribution of effects by carbon dioxide ($CO_2$) have led to researching ways to reduce $CO_2$ emissions. One solution is to capture $CO_2$ at its source (e.g., at a power plant) and sequestrate it before releasing to the atmosphere.

Conventional power plants use fossil fuel to generate power. Carbon dioxide is an inevitable byproduct of fuel-burning process. Conventional integrated gasification combined cycle (IGCC) power plants utilize clean coal power production, but their need for continuous supply of oxygen for combusting coal makes the construction and operation of such gasification power plant expensive limiting their scalability and reliability. In addition, as a result of partial combustion of coal with pure oxygen for heat production to drive the gasification reaction of coal, carbon dioxide is generated. The removal of carbon dioxide is required to achieve the required heating value of the produced Syngas.

The capital costs associated with oxygen production plants and gas cleaning equipment are roughly 25% of the entire gasification power plant. The production of oxygen and cleaning of combustion gases require energy. The more energy is produced, the more energy is spent for oxygen production and gas cleaning. Therefore, the operating cost for power generation using those conventional gasification system increases with their energy production capacity. This has an adverse affect on the overall efficiency and carbon dioxide emissions. Elimination of the oxygen plant not only lowers the capital costs of a clean coal power plant but also reduces carbon dioxide emissions.

SUMMARY

A system and method for providing an integrated indirectly fired reactor and steam generator are disclosed. According to one embodiment, the reactor comprises an indirect heating zone heating water and generating steam, a mixing zone mixing feedstock and the steam and providing a mixture of the feedstock and the steam, and a reaction zone comprising a first reactor and a second reactor. The first reactor converts the mixture to a first syngas at a first temperature. The second reactor converts the first syngas to a second syngas at a second temperature, the second temperature being higher than the first temperature.

The above and other preferred features, including various novel details of implementation and combination of elements, will now be more particularly described with reference to the accompanying drawings and pointed out in the claims. It will be understood that the particular methods and apparatuses are shown by way of illustration only and not as limitations. As will be understood by those skilled in the art, the principles and features explained herein may be employed in various and numerous embodiments.

BRIEF DESCRIPTION OF THE DRAWINGS

The accompanying drawings, which are included as part of the present specification, illustrate the presently preferred embodiment of the present invention and together with the general description given above and the detailed description of the preferred embodiment given below serve to explain and teach the principles of the present invention.

FIG. 5A is a top view of a cylindrical type reactor, according to one embodiment;

FIG. 5B is a top view of a box-type reactor, according to one embodiment;

Figure 1:
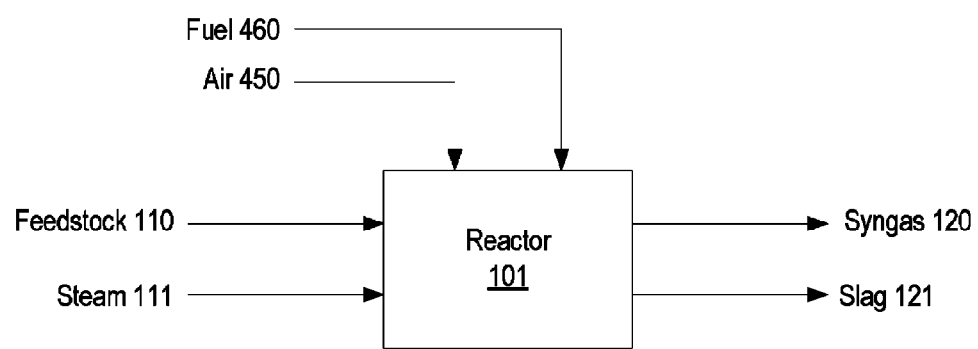
FIG. 1 illustrates a simplified process of oxygen-free gasification, according to one embodiment.

It should be noted that the figures are not necessarily drawn to scale and that elements of structures or functions are generally represented by reference numerals for illustrative purposes throughout the figures. It also should be noted that the figures are only intended to facilitate the description of the various embodiments described herein. The figures do not describe every aspect of the teachings described herein and do not limit the scope of the claims.

DETAILED DESCRIPTION

A system and method for providing an integrated indirectly fired reactor and steam generator are disclosed. According to one embodiment, the reactor comprises an indirect heating zone heating water and generating steam, a mixing zone mixing feedstock and the steam and providing a mixture of the feedstock and the steam, and a reaction zone comprising a first reactor and a second reactor. The first reactor converts the mixture to a first syngas at a first temperature. The second reactor converts the first syngas to a second syngas at a second temperature, the second temperature being higher than the first temperature.

In the following description, for purposes of clarity and conciseness of the description, not all of the numerous components shown in the schematic are described. The numerous components are shown in the drawings to provide a person of ordinary skill in the art a thorough enabling disclosure of the present invention. The operation of many of the components would be understood to one skilled in the art.

Each of the additional features and teachings disclosed herein can be utilized separately or in conjunction with other features and teachings to provide the present reactor. Representative examples utilizing many of these additional features and teachings, both separately and in combination, are described in further detail with reference to the attached drawings. This detailed description is merely intended to teach a person of skill in the art further details for practicing preferred aspects of the present teachings and is not intended to limit the scope of the claims. Therefore, combinations of features disclosed in the following detailed description may not be necessary to practice the teachings in the broadest sense and are instead taught merely to describe particularly representative examples of the present teachings.

Moreover, the various features of the representative examples and the dependent claims may be combined in ways that are not specifically and explicitly enumerated in order to provide additional useful embodiments of the present teachings. In addition, All features disclosed in the description and/or the claims are intended to be disclosed separately and independently from each other for the purpose of original disclosure, as well as for the purpose of restricting the claimed subject matter independent of the compositions of the features in the embodiments and/or the claims. All value ranges or indications of groups of entities disclose every possible intermediate value or intermediate entity for the purpose of original disclosure, as well as for the purpose of restricting the claimed subject matter. The dimensions and the shapes of the components shown in the figures are designed to help understand how the present teachings are practiced but are not intended to limit the dimensions and the shapes shown in the examples.

According to one embodiment, an integrated and indirectly fired oxygen-free gasification reactor for the production of steam and Syngas from coal, biomass or organic waste utilization is provided with effective removal of pollutants such as sulfur, mercury, and ash. The reactor may be used for the gasification of coal to syngas in an integrated gasification combined cycle (IGCC) process for power generation. Syngas is a mixture of gas with varying amounts of carbon monoxide (CO) and hydrogen gas ($H_2$).

The reactor may be used in combination with other processes for the production of transportation fuels, fertilizers and polymers. Unlike the existing gasification reactors, the present oxygen-free gasification reactors do not use oxygen. The elimination of an oxygen plant results in the reduction of capital costs, operational costs, reduction of $CO_2$ emissions, and increase in overall efficiency. Being oxygen-free, modular, and scalable, the present oxygen-free reactor provides low cost and clean energy production from coal, biomass, organic waste, or any other form of organic feedstock.

FIG. 1 illustrates a simplified process of oxygen-free gasification, according to one embodiment. The inside of a primary reaction chamber 404 of reactor 101 is maintained at temperature below 1000° C., and the inside of a secondary reaction chamber of reactor 101 is maintained at a temperature greater than 1000° C. and at a pressure in excess of 1 atmosphere. Organic matter 110 (e.g., coal or organic waste) and superheated steam 111 are supplied to reactor 101. Feedstock 110 (e.g., organic matter) is converted by endothermic chemical reaction with superheated steam ($H_2O$) to syngas 120 (i.e., mixture of carbon monoxide CO and hydrogen $H_2$) and byproduct 121 (e.g., sulfur or slag). Combustion of fuel 460 with air 450 generates heat for indirect heating to generate steam 111 and drive endothermic chemical reaction in reactor 101.

According to one embodiment, reactor 101 gasifies coal to syngas 120 in an integrated gasification combined cycle (IGCC) process for power generation. Reactor 101 may be used for conversion of biomass to syngas for producing transportation fuels. The processes of syngas production by reactor 101 may be applied for producing fertilizers and polymers.

Existing reactors for generating power, or for producing products (e.g., fuels, fertilizers, and polymers) require costly oxygen plants and do little to eliminate or reduce pollutants and other deleterious byproducts such as $CO_2$ and N. Reactor 101 does not require oxygen plants because the core reaction processes do not require oxygen. Reactor 101 eliminates pollutants and unwanted byproducts or reactants. Reactor 101, therefore, is significantly less expensive, cleaner, more efficient and reliable than existing reactors using oxygen.

Figure 2:
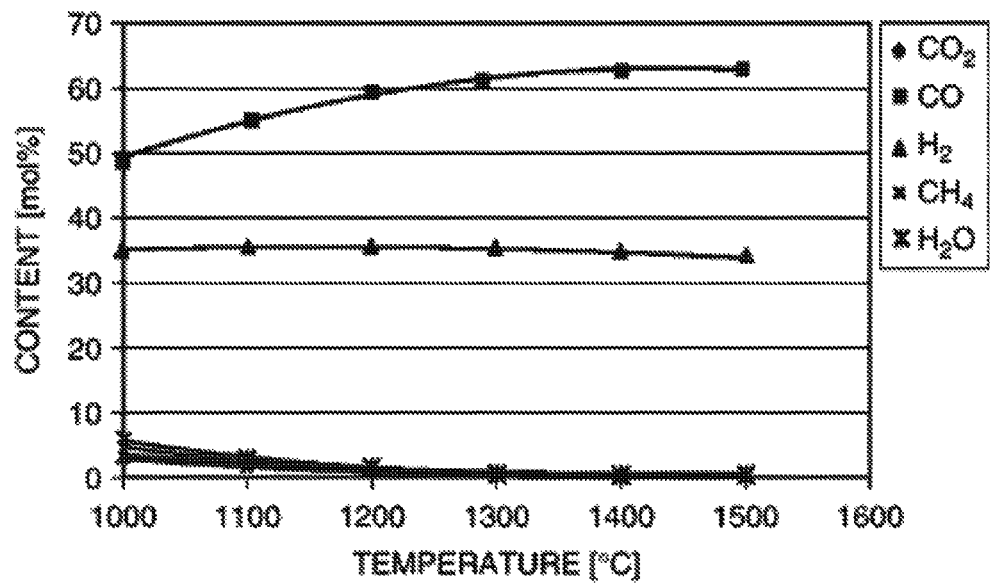
FIG. 2 illustrates a plot of exemplary syngas composition across a temperature range, according to one embodiment.

FIG. 2 illustrates a plot of exemplary syngas composition across a temperature range, taken from a publication entitled "Gasification" by Chris Higman and Maarten van der Burgt, (ISBN 0-7506-7707-4), which is incorporated herein by reference.

The pressure within primary reactor 404 is maintained at 30 bar. The syngas within reactor 101 contains gases such as hydrogen gas ($H_2$), carbon dioxide ($CO_2$), methane ($CH_4$), and steam ($H_2O$). The content of $CO_2$ and $H_2$ in syngas exceeds 80% at temperatures over 1000° C. As the temperature within primary reactor 404 increases, the content of CO increases while that of $H_2$, $CO_2$, $CH_4$, and $H_2O$ decreases.

Figure 3:
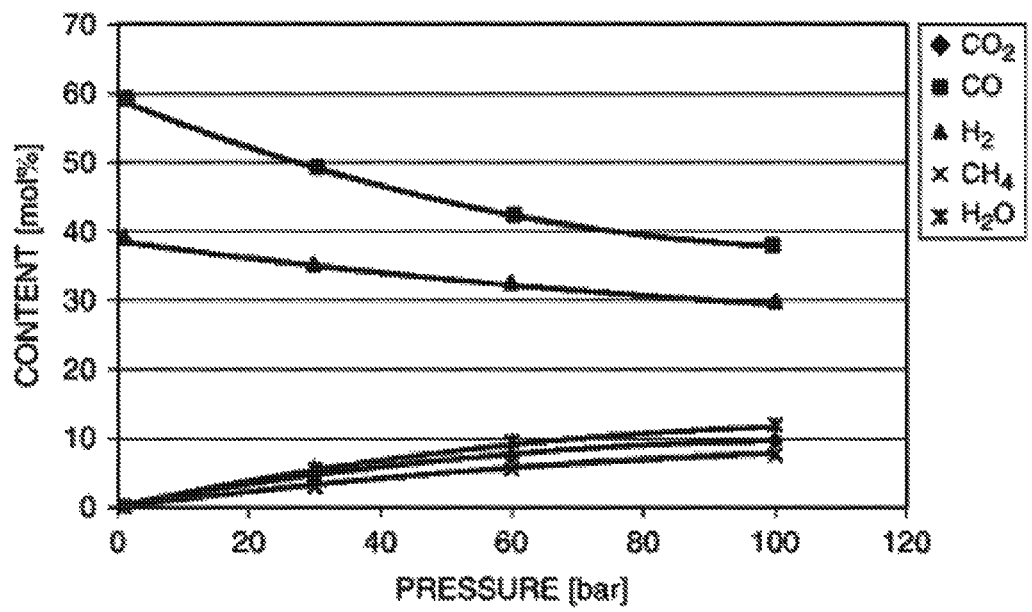
FIG. 3 illustrates a plot of exemplary syngas composition over a pressure range, according to one embodiment.

FIG. 3 illustrates a plot of exemplary syngas composition over a pressure range, taken from a publication entitled "Gasification" by Chris Higman and Maarten van der Burgt, (ISBN 0-7506-7707-4), which is incorporated herein by reference. The temperature within primary reactor 404 is maintained at 1000° C. As the pressure within primary reactor 404 increases, the content of CO and $H_2$ decreases while the content of $CO_2$, $CH_4$, and $H_2O$ increase.

Figure 4:
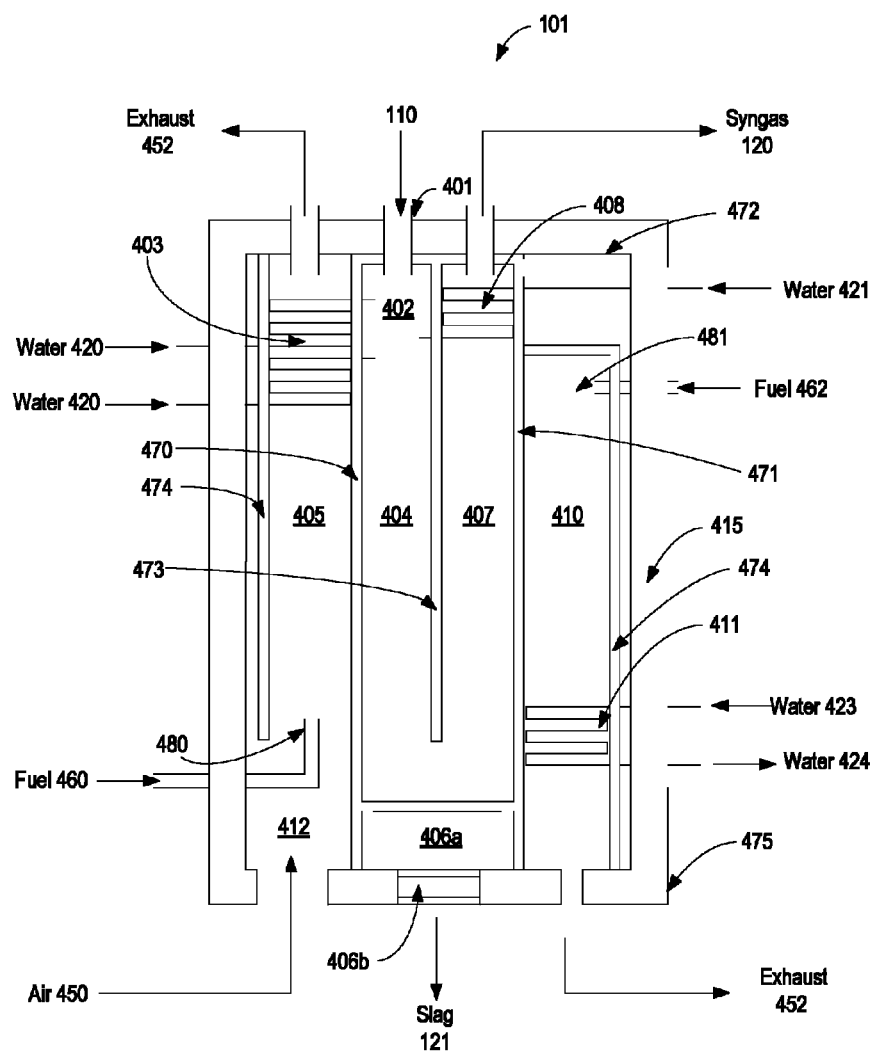
FIG. 4 illustrates an exemplary oxygen-free gasification reactor, according to one embodiment.

FIG. 4 illustrates an exemplary oxygen-free gasification reactor, according to one embodiment. Feedstock 110 (e.g., pulverized coal, petroleum coke, oil sands, biomass, organic waste) is fed through a swirling nozzle in feed injection zone 401 and mixed with superheated steam 111 generated by steam generators 403 and 408 in mixing zone 402. Reactor 101 may process slurry, dry solids, or other types of feedstock. To achieve higher efficiency, feedstock may be mixed with $CO_2$. If dry pulverized coal is forcefully injected under high pressure with $CO_2$, the amount of heat needed to increase the temperature of the carrying water to steam is eliminated from the overall energy requirement. This increases the overall efficiency.

Feedstock 110 is injected at a high pressure vertically downward in the direction of gravity and mixed with superheated steam 111 in a cross-flow pattern as illustrated in FIG. 4. In preheating zone 405 (also referred to herein as a heating zone and a preheating zone), syngas or startup fuel 460 is combusted with air 450 to produce the required heat in primary reactor 404 and generate hot combustion gases therein. Superheated steam 111 is generated by gas-to-liquid heat exchanger 403 using the hot combustion gases in preheating zone 405. Superheated steam 111 is provided by jets to create sufficient turbulence in mixing zone 402 and is mixed with feedstock 110 prior to entering primary reactor 404.

According to one embodiment, reactor 101 has a high surface area to volume ratio such that feedstock 110 undergoes gasification as a result of thermally driven gasification reaction in reactor 101. For example, for a given internal volume of reactor 101, the surface area inside reactor 101 is increased using protruded structures such as fins or rods thermally connected to the inner walls of reactor 101. As the mixture of feedstock 110 and superheated steam 111 moves downward, solid-gas reaction occurs as it reaches the bottom of primary reactor 404. The resulting gases make a u-turn and enter secondary reactor 407. Un-gasified solids are periodically recovered from recovery zone 406. The temperature of primary reactor 404 is regulated and maintained below slag melting temperature to avoid fouling. The fouling temperature is determined by various conditions such as the type of feedstock 110, the composition of feedstock 110, the type of reactants mixed with feedstock 110, and the type of reactions in the reaction chambers.

According to one embodiment, a different series of reactions may occur depending on the type of feedstock 110 fed to reactor 101 and the type of reactants mixed with feedstock 110. The temperatures in primary reactor 404 and secondary reactor 407 may be maintained at different temperatures to facilitate and control the series of reactions. Depending the type of reactions occurring in primary reactor 404 and secondary reactor 407, a solid, liquid, or gas product may be recovered or extracted therefrom. The recovered liquid or gas exits through recovery zone 406.

According to one embodiment, heat pipes with high thermal conductivity are provided between heating zones 405 and 410 and reactor cores 404 and 407. The heat pipes transfer heat from heating zones 405 and 410 to reactor cores 404 and 407 to sustain an endothermic reactor process in the reactor cores 404 and 407. In one embodiment, heat pipes are made of Molybdenum and filled with liquid Lithium. The heat pipes have a diameter of about 50-100 mm to transport heat over several meters.

According to another embodiment, thermal pipes encompassing heating zones 405 and 410 and reactor cores 404 and 407 have protruded structures such as fins or rods on their surfaces to maximize heat absorption and radiation. The heat pipes may be welded to the walls of chambers 404, 405, 407, and 410 and the fins or rods.

According to one embodiment, the primary reactor 404 converts the organic components of the mixture of feedstock 110 and steam 111 to gaseous mixture for the separation and removal of inorganic solids such as silicate minerals at a lower temperature. The secondary reactor 407 drives the syngas reactions further to completion and removes methane and water to increase the quality of the syngas at a higher temperature over 1000° C.

According to one embodiment, preheating zone 405 has a high surface area to volume ratio to effectively transfer significant amounts of heat to primary reactor 404 across dividing wall 470. The hot gases leaving preheating zone 405 heat second heat exchanger 408 to generate more superheated steam 111 to accelerate gasification in mixing zone 402. The preferred temperature of steam is about 500° C.

According to one embodiment, recovery zone 406 is compartmentalized to transfer the residual solids from the reactor core 404 and 407 outside reactor 101. An outer compartment 406b is evacuated from atmosphere prior to opening to an inner compartment 406a to prevent any significant amount of air from entering reactor cores 404 and 407. The low pressure created in the outer compartment 406b causes rapid transfer of the residual solids when the inner compartment 406a to the reactor cores 404 and 407 are closed and the outer compartment 406b is opened. The process of solid transfer takes place periodically depending on the type feedstock being processed in reactor 101. The preferred period for solids removal is set from energy and mass balance on reactor 101, for example, based on the overall size, type of feedstock 110 and the processing rate of reactor 101.

According to one embodiment, secondary reactor 407 has a high surface area to volume ratio to facilitate heat transfer from primary reactor 404 across dividing wall 470. The gases in secondary reactor 407 experience a higher temperature than that of primary reactor 404 as a result of being in countercurrent flow and heat transfer from the heat generated by the combustion of fuel 462 with air 450 in heating zone 410, driving stronger reactions therein. The higher temperature in secondary reactor 407 increases the concentration of CO and $H_2$ but decreases that of $CH_4$ and $CO_2$, which is the desired outcome. The hot gases leaving secondary reactor zone 407 enter second steam generation zone 408 to produce additional steam in mixing zone 402.

In case of coal gasification, reactor 101 removes un-gasified solids by the temperature differences between primary reactor 404 and secondary reactor 407. In other cases, no solids may be removed during the transition from primary reactor 404 and secondary reactor 407, but other forms of multi-stage reactions may occur therein due to the indirect but controlled heating process in heating zones 405 and 410. For example, primary reactor 404 produces a certain product at a first temperature, and a different reaction occurs in secondary reactor 407 that is maintained in a second temperature. The product of primary reactor 404 may be separated before exiting primary reactor 404. The product of secondary reactor 407 may only be produced as a result of the production and/or removal of the first product in primary reactor 404.

Depending on the type of reactions occurring in primary reactor 404 and secondary reactor 407, the material of the reactors/heat exchangers does not have to have high melting point but required to have a high thermal conductivity such as that of copper and aluminum. For an application that requires the temperature of primary reactor 404 be maintained at less than 100° C. and the temperature of secondary reactor 407 be maintained between 200-400° C., the reactors/heat exchangers can be made of aluminum. For another application, copper can be used if the temperatures inside primary reactor 404 and secondary reactor 407 are to be maintained at 600° C., and 650-1000° C., respectively.

According to one embodiment, heat exchangers 403 and 408 are used to cool the generated syngas 120 to a temperature suitable for downstream gas cleaning processes. The cleaned syngas 632 may be fed into a gas turbine for power generation applications.

In heating zone 410, syngas or startup fuel 462 is combusted with air 450 to produce heat for gas-solid reactions in primary reactor 404 and secondary reactor 407. The secondary heat exchanger 408 uses the heat produced by fuel 462 and air 450 and produce additional superheated steam 111. Heating zone 410 has a high surface area to volume ratio to effectively transfer heat to reaction zones 404 and 407 across the dividing wall 471.

Superheated steam 111 is generated by gas-to-liquid heat exchangers 403 and 408 using the combustion gases from heating zones 405 and 410. According to one embodiment, the hot gases leaving heating zone 410 enter third steam generation zone 411 to drive a steam turbine for power generation.

According to one embodiment, various feeding systems are employed based on the type of feedstock. In one example, conventional slurry feeders may be used to dry feed the feedstock (e.g., pulverized coal, petroleum coke, or oil sands) with $CO_2$ and mix with steam generated by the combustion products of the preheating and heating processes in preheating zone 405 and heater 410. An example of a standard slurry feeder is GEHO® PD slurry pump manufactured by Weir Group PLC of United Kingdom. In another example, biomass or waste may be fed with a piston or a screw type feeder.

According to one embodiment, reactor core walls 472 are made of material with the following properties:
thermal conductivity greater than 80 W/m ° C.;
chemically inert in the carbon monoxide and hydrogen environment; and high melting point to withstand the heat of combustion in preheating zone 405 and heater 410, for example, greater than 2500° C.

Reactor core walls 472 must withstand the internal pressure of reactor cores 404 and 407. To maximize thermal conductivity, reactor core walls 472 may be fabricated into enclosed structures with larger surface area such as the heat radiating surfaces of heat exchangers 403 and 408 and pressure chambers 404, 405, 407, and 410. In one example, Molybdenum Alloy TZM is used for building reactor core walls 472 and heat exchangers 403 and 408. Reactor 101 may be used for other processes and applications without requiring high temperature for reaction. In this case, a different construction material may be used.

The size and capacity of heat exchanger 403 may be determined based on the overall design and capacity of reactor 101. According to one embodiment, heat exchanger 403 is a Bowman® exhaust gas heat exchanger manufactured by E. J. Bowman Limited of Birmingham, England. In another embodiment, heat exchanger 403 may be a direct firing heat exchanger if the waste heat recovered from preheating zone 405 is not sufficient for generating superheated steam 111. In yet another embodiment, heat recovery from the exhaust gas of preheating zone 405 is supplemented with a direct firing heat exchanger to generated superheated steam 111.

According to one embodiment, reactor core dividing wall 473 is made from the same material as the reactor core walls 470 and 471. The dimensions of reactor core dividing wall 473 are determined based on the overall design and optimization of reactor 101.

A smaller dimension of reactor 101 is preferred. The main design objective for reactor 101 is to achieve the highest ratio of surface area to volume for a given reactor capacity. The science and the art to be applied in the design and optimization of a reactor is well know in the art and documented in several manuals and books for heat exchanger design, for example, "Compact Heat Exchangers" authored by W. M. Kays and A. L. London. In this case, a countercurrent heat exchanger design may be applied. Reactor core dividing wall 473 provides a barrier and thermal coupling between primary reactor 404 and secondary reactor 407. Efficient thermal coupling between primary reactor 404 and secondary reactor 407 is achieved through the extended surface area of reactor core dividing wall 473. In one embodiment, the extensions of the surface area of reactor core dividing wall 473 are achieved by fin extensions 483.

According to one embodiment, primary reactor 404 is made of a large number of fins to increase the surface area to volume ratio. Depending on the type of feedstock that reactor 101 processes, the dimensions and sizes of fins may vary. For example, fin extensions are made of sheets extending along the chamber of primary reactor 404, or rods connected across wall 470 separating preheating zone 405 and primary reactor 404. The rods may or may not interface directly with the fins of preheating zone 405.

According to one embodiment, primary reactor 404 initiates a primary stage in the process where the temperature is lower. The design and concept of reactor 101 may be applied to other processes where indirect heating drives multi-stage reaction. In the primary stage, feedstock is gasified at a lower temperature to remove the solids. In a subsequent process, a certain reaction is activated at a given temperature range. For gasification of coal, operation at a lower temperature below which recovery and extraction of softened and agglomerated ash from primary reactor 404 is eased. Devolatilization of coal takes place in the rage of 350-800° C. In this embodiment, the temperature of primary reactor 404 is kept below 1000° C. As a result, all of the ash is separated from the coal while the softening and/or melting of the ash is prevented. For solid feedstock such as coal, ash content may vary from 2.7% to 40% by mass. Primary reactor 404 and preheating zone 405 are designed and optimized for specific types of feedstock, and the devolatilization and ash separation/extraction processes are controlled accordingly.

According to one embodiment, preheating zone 405 is made of a predetermined number of fins to obtain a particular ratio of fin surface area to chamber volume. The ratio is related to the thermal coupling capacity between preheating zone 405, and steam generators 403 or the neighboring primary reactor 404. The fins of preheating zone 405 may be made from a material of high thermal conductivity. The fins are thermally welded to reactor core wall 470. Thermal rods or sheets may be coupled to reactor core wall 470 to function as fins. These thermally coupling internal structures may extend across reactors 405, 404, 407, and 410. The configuration and density of thermally coupling internal structures may vary depending on the design of reactor 101 and conditions for the intended gasification processes.

Due to the high temperature (e.g., 1800° C.) inside preheating zone 405 and heater 410, radiation through surrounding walls is a significant cause of heat transfer. To minimize heat loss, thermal radiation shield 474 is placed between refractory brick lining 415 of reactor 101, and preheating zone 405 and heater 410. Thermal radiation shield 474 is made of a layer of refractory lining such as $Al_2O_3$ or other thermally insulating material. Thermal radiation shield 474 is separated from refractory brick lining 415 of reactor 101 and reactor walls and fins by a layer of air to reduce thermal conduction with refractory brick lining 415.

Conventional gasification reactors do not have thermal radiation shield 474. With conventional reactors, the inner surfaces of the refractory lining are the lining of the reactor. Thus, the reactants are directly in contact with the inner surface of a refectory brick lining.

According to one embodiment, refractory brick lining 415 of reactor 101 is chemically insulated from both the combustion gases exiting from preheating zone 405 and heater 410 and the atmosphere inside the reactor cores (i.e., primary reactor 404 and secondary reactor 407).

For producing syngas, the atmosphere inside the reactor core is highly reducing—the oxide material of refractory brick lining 415 (e.g., $Al_2O_3$, $Fe_2O_3$, MgO, CaO) reacts with CO and $H_2$ to produce $CO_2$, $H_2O$ and basic metals such as Fe, Ca, Mg, and Al. The constant chemical attack by the CO and $H_2$ in the syngas affects service life of refractory brick lining 415, and may result in a shutdown for repair. Reactor walls 470 and 471 eliminate direct contact of syngas with refractory brick lining 415 and allows for containment of the syngas in the chemically-inert reactor cores.

According to one embodiment, preheating burners 480 and 481 combust fuels 460 and 462 such as natural gas or syngas. The capacity and placement of preheating burners 480 and 481 are determined by the design configuration of reactor 101 to provide heat for primary reactor 404 and secondary reactor 407 and generate superheated steam 111. Combustion of fuels 460 and 462 may be driven by air or oxygen. When air is used, some of the air is supplied as primary air for combustion of fuels 460 and 462 and the remaining air is induced through an air inlet as a result of the negative pressure created by exhaust 452.

Splitting the combustion air into primary injected through burner 480 and secondary induced by a jet of the flame at burner 481 enables the precise control of the flame shape and length. The induction strength for the secondary air is driven by the amount of negative pressures which may be created by the downstream fluid moving equipment such as a blower or fan. In this case, the induction fan or blower would be located downstream of heat exchangers 403, 408, and 411. If oxygen is used, the exhaust gas is injected into reactor 101 to drive the flow of solids and ultimately to capture and sequestrate $CO_2$. Heating burners 480 and 481 may be a single burner or multiple burners. Heating burners may be positioned vertically (e.g., burner 480) where the flame is penetrating up through the fins or horizontally (e.g., heating burner 481). It is appreciated that different configurations of burners 480 and/or 481 are possible without deviating from the scope of the present subject matter.

According to one embodiment, solid byproducts such as high ash content coal or oil sands are cooled using a bed cooler. Secondary air zone 412 may be a solid bed cooler wherein the secondary air flows in to cool the ash, sand, or slag, and recover residual heat in the solids.

According to one embodiment, secondary reactor 407 is made of a predetermined number of fins to obtain a particular ratio of fin surface area to chamber volume. The ratio is related to the thermal coupling capacity between secondary reactor 407 and neighboring primary reactor 404 and heater 410. According to one embodiment, secondary reactor 407 is maintained at a temperature higher than primary reactor 404 (e.g., 1200° C. or higher), to effectuate high temperature gas-phase reactions. At a temperature higher than 1000° C., the ratio of $CO+H_2$ with respect to $CH_4+CO_2$ is higher, so that higher quality syngas is produced.

According to one embodiment, the outer surface of refractory brick lining 415 is covered with shell 475. The thickness and material of shell 475 is determined to sustain high temperature within reactor 101 and to provide structural rigidity of reactor 101. In one embodiment, shell 475 is made of steel. The preferred thickness of shell 475 is 15-30 mm.

Unlike conventional gasification reactors, the internal cavity of reactor 101 contains heavily integrated metallic structures. The internal structures may be built on a steel base.

According to one embodiment, reactor 101 starts with syngas or startup fuel (e.g., natural gas) to heat preheating zone 405 and heater 410. As the temperature of the reactor cores 404 and/or 407 reaches to a desired temperature (e.g., higher than 1500° C.), water (e.g., 420, 421, 423) is introduced into reactor 101 for steam generation, and feedstock (e.g., slurry or dry coal) is injected into reactor 101. The feed rates including the water flow rates to the reactor core 404 and fuel flow rates to burners 480 and 481 are adjusted until the concentrations of $H_2$, CO, $H_2O$, $CO_2$ and $CH_4$ in the product (syngas) approach the desired values. According to one embodiment, the feed rates and fuel flow rates are measured with sensors and computer controlled. As the steam generation rate approaches a predetermined level for a specific reactor and/or the entire plant mass-and-energy balance, the superheated steam may be fed to a turbine for power generation in the case of power generation reactor 101. The composition of syngas is monitored. After the composition of syngas is reached to a desired level, the syngas is sent to turbine and/or storage tanks. An ideal syngas is made only of CO and $H_2$. A plant/reactor designer sets the desired syngas quality based on the overall optimization of reactor and efficiency of the plant being designed. The design and optimization of such reactors and plants are well known to the practitioners of the art.

FIG. 5A is a top view of a cylindrical type reactor, according to one embodiment. The cylindrical type reactor 501 is covered with refractory brick lining 515 and shell 575. Primary reactor 504 and secondary reactor 507 are contained in reactor core walls 572, shielded from refractory brick lining 515 by radiation shield 574. Dividing wall 570 separates primary reactor 504 and secondary reactor 507.

FIG. 5B is a top view of a box-type reactor, according to one embodiment. The box-type reactor 101 is covered with refractory brick lining 415 and shell 475. Primary reactor 404 and secondary reactor 407 are contained in reactor core walls 472, shielded from refractory brick lining 415 by radiation shield 474. Dividing wall 470 separates primary reactor 404 and secondary reactor 407.

According to one embodiment, syngas is used for producing fertilizers, or other types of products. Nitrogen is a basic component of air, thus is desirable for making fertilizers whose basic chemical compounds is ammonium nitrate ($NH_4NO_3$). If oxygen is used, the exhaust gases made of $CO_2$ and $H_2O$ are used as a gasification moderator to control the ratio of CO with respect to $H_2$ in the syngas. The more water (steam) is added to the feedstock, the higher is the hydrogen content of the syngas. However, adding water however reduces the thermal efficiency. A controlled amount of water and carbon dioxide may be added to regulate the ratio of CO and $H_2$. The recycling of hot exhaust gases in the feeder for injecting feedstock (e.g., pulverized coal) significantly increases the efficiency and enables dry feed. Dry feed does not contain water which requires additional heat to increase its temperature to generate steam. Reduction of the externally provided energy achieves the increase of the overall efficiency of reactor 101.

According to one embodiment, $CO_2$ injected with pulverized coal reacts with the coal according to the Boudouard reaction and produces CO and heat energy, as given below:

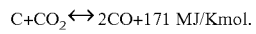

$$C+CO_2 \leftrightarrow 2CO+171 \text{ MJ/Kmol}.$$

This reaction is an endothermic reaction that requires heat to drive formation of CO. Reactor 101 allows for the adjustment of heat added for reaction by adjusting the heating rates from burners 480 and 481.

The integrated design of reactor 101 enables higher efficiency than conventional gasification reactors. Because the source of heat is external to primary reactor 404 and secondary reactor 407, $CO_2$ generated as a byproduct of gasification is sequestrated without adversely affecting the stability of reactor 101, $H_2O$ in the exhaust of preheating zone 405 and heater 410 are recycled for heat recovery. A greater degree of moderation for the ratio of CO versus $H_2$ in the syngas is obtained.

In addition, steam can be injected at a variable rate to increase hydrogen concentration in the syngas. This is not easily achievable in conventional gasification reactors because the increase of steam to the internal source of heat can cause instability within the reactors 405 and/or 407.

Figure 6:
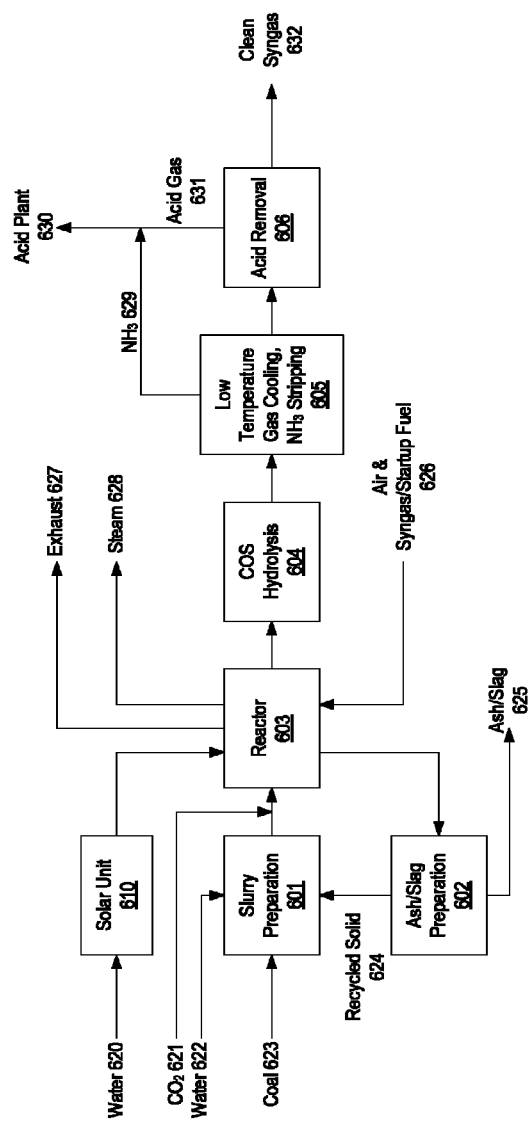
FIG. 6 illustrates a block diagram for an exemplary integrated gasification combined cycle, according to one embodiment.

FIG. 6 illustrates a block diagram for an exemplary integrated gasification combined cycle, according to one embodiment. For a dry feed application, coal 623 is fed without water 622 and is mixed with $CO_2$ 621 in a slurry preparation block 601. The mixture of coal and $CO_2$ 621 is fed to reactor 603 for generating power. The high pressured steam 628 generated in reactor 603 as a result of gasification drives a turbine. The $CO_2$ in exhaust gas 627 from reactor 603 is captured and sequestrated. The mixture of syngas or startup fuel with air 626 to heat preheating zone 405 and heater 410. Syngas generated in reactor 603 is sent to a COS hydrolysis unit 604 for absorption. COS hydrolysis units are well known in the art, thus the details of which will not be discussed herein. Syngas passed to COS hydrolysis unit 604 is further processed for cooling and ammonia ($NH_3$) stripping (e.g., $NH_3$ stripping unit 605). The syngas is further processed to extract acid gas 631 (e.g., sulfuric acid) (e.g., acid stripping unit 606). The ammonia gas 629 stripped by $NH_3$ stripping unit 605 and sulfuric gas stripped by acid stripping unit 606 are fed to a processing plant 630. The cleaned syngas 632 may be used to drive a turbine.

According to one embodiment, reactor 603 is integrated with a solar unit 610 to preheat water 620 and/or generate steam 111 that is fed to reactor 603.

Figure 7:
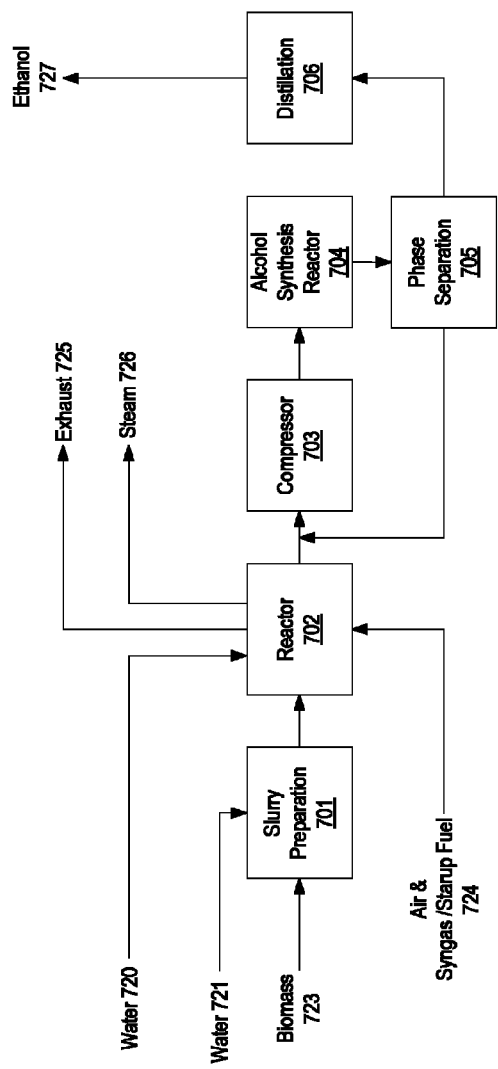
FIG. 7 illustrates a block diagram for an exemplary biomass to ethanol conversion, according to one embodiment.

FIG. 7 illustrates a block diagram for an exemplary biomass to ethanol conversion, according to one embodiment. The mixture of biomass 723 and water 721 is fed to a slurry preparation block 701 and subsequently reactor 702. The high pressured steam 726 generated in reactor 702 as a result of gasification drives a turbine. The $CO_2$ in exhaust gas 725 from reactor 702 is captured and sequestrated. Syngas generated in reactor 702 is fed to compressor 703 and subsequently fed to alcohol synthesis reactor 704. The liquefied alcohol is processed for phase separation by phase separation unit 705 and distilled at distillation unit 706 to produce ethanol 727. The distilled ethanol 727 is used as an alternative fuel to fossil fuels (e.g., gasoline, natural gases). The process of coupling a gasifier or a syngas production reactor disclosed herein with a process, for example a Fischer-Tropsch process, for the production of synthetic fuels and chemicals is well known and widely practiced.

According to one embodiment, reactor 702 is equipped with various sensors and meters, for example a mass flow meter, a pressure sensor, a temperature sensor, and a mixture sensor. These sensors and meters are to be placed in locations of the highest and lowest expected values to be monitored, to measure the mass flow rate, temperature, pressure and species concentration of all of the inlet and outlet streams in the reactor. The sensor outputs are fed to a main computer for dynamic data monitoring, processing, and control. In one embodiment, startup and steady state operating conditions are determined from the calculation of an energy-and-mass balance process and stored in the main computer for dynamic monitoring and adaptive control. The reactor control system may interface with another control system and designed to be integrated with other reactors and/or plants.

While the present system has been shown and described herein in what is considered to be the preferred embodiments thereof, illustrating the results and advantages over the prior art obtained through the present invention, the invention is not limited to the specific embodiments described above. Thus, the forms shown and described herein are to be taken as illustrative, and other embodiments may be selected without departing from the spirit and scope of the present subject matter.

Embodiments as described herein have significant advantages over previously developed implementations. As will be apparent to one of ordinary skill in the art, other similar apparatus arrangements are possible within the general scope. The embodiments described above are intended to be exemplary rather than limiting, and the bounds should be determined from the claims.

What is claimed is:

1. A method for providing oxygen-free gasification in a system, comprising:
combusting syngas with air in an indirect heating zone to generate hot combustion gases, the indirect heating zone having a heat exchanger for generating steam by using the hot combustion gases;
heating a reaction zone by using the hot combustion gases for heating a reaction zone;
mixing feedstock and the steam in a mixing zone; providing, by the mixing zone, a mixture of the feedstock and the steam; and
performing oxygen-free gasification in the reaction zone, wherein oxygen-free gasification comprises
converting, in a first reactor, the mixture to a first syngas at a first temperature; and converting, in a second reactor, the first syngas to a second syngas at a second temperature, the second temperature being higher than the first temperature, wherein the hot combustion gases remain separated from the steam, the feedstock, the mixture, the first syngas, and the second syngas.

2. The method of claim 1, wherein the reaction zone is surrounded by the heating zone.

3. The method of claim 1, wherein the first reactor is one of a cylindrical shape or a rectangular shape.

4. The method of claim 1, wherein the first reactor and the second reactor are vertically disposed next to each other and are separated by a dividing wall.

5. The method of claim 1, wherein a plurality of thermal conductors extends from the heating zone to the first reactor and the second reactor.

6. The method of claim 1, wherein the heating zone comprises a first heating zone disposed adjacent to the first reactor and a second heating zone disposed adjacent to the second reactor.

7. The method of claim 1, wherein the mixing zone comprises a feed injection zone and the feedstock is gravity-fed via the feed injection zone.

8. The method of claim 1, further comprising mixing the feedstock with $CO_2$.

9. The method of claim 1, further comprising mixing the feedstock with the steam in the mixing zone in a cross-flow pattern.

10. The method of claim 1, further comprising providing the steam in the form of jets and creating turbulence in mixing zone.

11. The method of claim 1, further comprising collecting, by a compartmentalized recovery zone, residual solid, liquid, or gas generated in the reaction zone.

12. The method of claim 11, wherein the recovery zone comprises an inner compartment and an outer compartment, and wherein air in the outer compartment is evacuated prior to opening the inner compartment to prevent the air from entering the reaction zone.

13. The method of claim 1, wherein a refractory brick lining surrounds the first or second reactor.

14. The method of claim 13, wherein a thermal radiation shield is disposed between the refractory brick lining and the heating zone.

15. The method of claim 1, wherein the second syngas comprises $CO_2$.

16. The method of claim 15, wherein the $CO_2$ is fed for capture and sequestration.

17. The method of claim 15, wherein the second syngas further comprises hydrogen sulfide.

18. The method of claim 17, further comprising extracting the hydrogen sulfide from the second syngas.

19. The method of claim 17, further comprising driving a turbine for power generation by using the second syngas.

20. The method of claim 1, wherein the feedstock is biomass.

21. The method of claim 20, wherein the system further comprising a compressor and an alcohol synthesis reactor.

22. The method of claim 20, further comprising producing, by a distiller, ethanol from the syngas.

23. The method of claim 1, further comprising feeding the second syngas to a synthesis reactor to generate synthetic fuels.

\* \* \* \* \*